United States Patent [19]

Dhaliwal

[11] 3,980,640
[45] Sept. 14, 1976

[54] SCHIFF BASES DERIVED FROM PHENANTHRENE-9,10-DIAMINES AND ORTHO-HYDROXY ALDEHYDES

[75] Inventor: Pritam Singh Dhaliwal, Edison, N.J.

[73] Assignee: E. I. Du Pont de Nemours and Company, Wilmington, Del.

[22] Filed: June 13, 1975

[21] Appl. No.: 586,745

Related U.S. Application Data

[62] Division of Ser. No. 535,140, Dec. 20, 1974, Pat. No. 3,928,328, which is a division of Ser. No. 313,359, Dec. 8, 1972, Pat. No. 3,903,118.

[52] U.S. Cl. .................. 260/240 G; 260/429 C; 260/438.1; 260/439 R; 260/566 F
[51] Int. Cl.² ........................................ C07C 119/00
[58] Field of Search ........ 260/566 F, 566 R, 240 G, 260/429 C, 438.1, 439 R

[56] References Cited

UNITED STATES PATENTS

| | | | |
|---|---|---|---|
| 3,290,299 | 12/1966 | Kumins et al. | 260/240 G |
| 3,441,578 | 4/1969 | Dimroth | 260/429 |
| 3,687,991 | 8/1972 | Gaeng et al. | 260/429 C |
| 3,864,371 | 2/1975 | Inman et al. | 260/439 R |

*Primary Examiner*—Gerald A. Schwartz

[57] ABSTRACT

Novel Schiff bases are prepared by condensation of phenanthrene-9,10-diamines with o-hydroxy aldehydes. The bases can be chelated with metals to form compounds useful as yellow pigments.

1 Claim, No Drawings

SCHIFF BASES DERIVED FROM PHENANTHRENE-9,10-DIAMINES AND ORTHO-HYDROXY ALDEHYDES

CROSS-REFERENCE TO RELATED APPLICATIONS

This application is a division of application Ser. No. 535,140, filed Dec. 20, 1974, Pat. No. 3,928,328, issued 12-23-75, which in turn is a division of application Ser. No. 313,359, filed Dec. 8, 1972, Pat. No. 3,903,118, issued 9-2-75.

BACKGROUND OF THE INVENTION

Although a number of lightfast organic pigments have been developed in the blue to green color range, as exemplified by the phthalocyanines, and in the red to violet range, as exemplified by the quinacridones, there has been much less success with the development of such pigments in the yellow range. The present invention is directed to the production of novel yellow organic pigments.

SUMMARY OF THE INVENTION

This invention relates to new compounds which are Schiff bases and to their metal chelate derivatives. As pigments the latter possess outstanding durability, and are distinguished by their stability to heat, extreme light-fastness and bleed resistance.

The Schiff bases of the invention are prepared by the condensation of a phenanthrene-9,10-diamine with an o-hydroxy aldehyde to yield colored Schiff bases according to the following reaction:

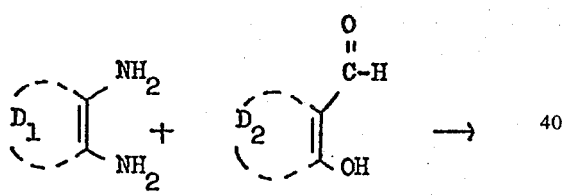

(I)         (II)

wherein $D_1$ represents the atoms necessary to complete a phenanthrene nucleus having the indicated nitrogen atoms attached to the 9,10-positions and $D_2$ represents the atoms necessary to complete a nucleus of the formula:

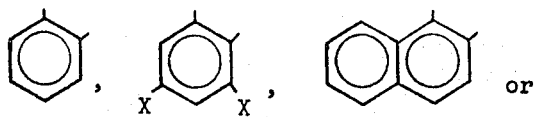

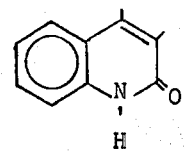

wherein X is chlorine or bromine.

The metal chelate derivatives have the formula:

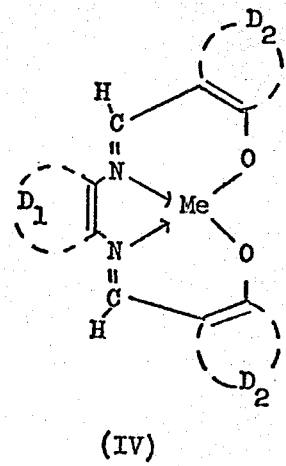

(IV)

wherein Me is nickel, cobalt or copper and $D_1$ and $D_2$ are as given before.

For the preparation of the Schiff bases and the chelates of the invention, phenanthrene-9,10-diamines of the formula:

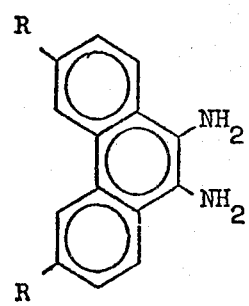

wherein R is hydrogen, chlorine or bromine, are preferred. Other substituents may be present on the phenanthrene moiety, however, for example, lower alkyl radicals such as methyl and ethyl, and alkoxy radicals such as methoxy.

The o-hydroxy aldehydes that may be employed include salicyl aldehyde; 3,5-dibromo- and 3,5-dichlorosalicylaldehyde; 2,4-dihydroxy-3-formyl-quinolinoline; and 2-hydroxy-1-naphthaldehyde. The preferred compound is 2,4-dihydroxy-3-formylquinoline which, when condensed with phenanthrene-9,10-diamine and chelated yields a compound of the formula:

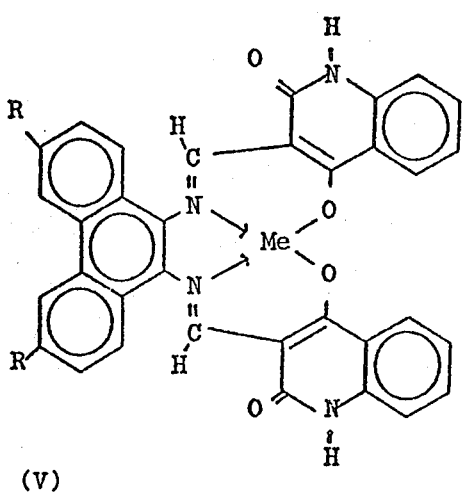

(V)

wherein each R is hydrogen.

The Schiff bases of this invention are produced by condensing two moles of the o-hydroxy aldehyde with one mole of phenanthrene-9,10-diamine or a substituted derivative of the latter. The Schiff base is further reacted with a nickel, cobalt or copper salt, such as for example nickel acetate, to give a highly insoluble reddish-yellow compound having exceptional lightfastness and other valuable pigmentary properties, i.e., to give the chelate.

The condensation of the o-hydroxy aldehyde with the phenanthrene-9,10-diamine can be carried out in a variety of polar solvents. It is found that the reaction proceeds readily in acidic aqueous medium (pH 3–5), butanol, ethanol, and dimethylformamide. However, if desired, other solvents such as, for example, propanol, ethylene glycol or the like, may be used with equal success.

The metal complexes can be conveniently formed by reacting the Schiff base with a metal salt of an organic acid in suspension in a high-boiling solvent such as demethylformamide, dimethylacetamide, dimethylsulfoxide, tetramethylene sulfone and the like. Although for purposes of illustration nickel acetate is the metal salt used and is preferred, salts of the metals cobalt or copper may be substituted. Salts other than acetates can be used, provided they are sufficiently soluble in the solvent used in carrying out the chelation reaction. Since the condensation to form the Schiff base can also be carried out in a high-boiling polar solvent such as demethylformamide or one of the other solvents listed above, the formation of both the Schiff base and the metal complex can be carried out in succession in the same reaction medium without isolation of the Schiff base intermediate.

To illustrate in detail the preparation of the compounds of the invention, the following examples are given. These are intended to be illustrative only and are not to be held as in limitation of the invention.

EXAMPLE 1

A. Synthesis of Schiff base from 2,4-dihydroxy-3-formylquinoline and phenanthrene-9,10-diamine Ten grams of phenanthrene-9,10-diamine and 21.5 grams of 2,4-dihydroxy-3-formylquinoline are refluxed in 1800 ml butanol for five hours. The slurry is filtered hot and the presscake washed with alcohol and dried. The bright yellow Schiff base product weighs 22.5 grams.

B. Formation of nickel chelate

Fifteen grams of the Schiff base product of A and 10.0 grams nickel acetate tetrahydrate are heated at reflux in 1800 ml N,N'-dimethylformamide for four hours. The slurry is filtered hot and the presscake washed successively with dimethylformamide, alcohol and water, and dried at 60°C. The yield of product is 14.6 grams.

The chelate product is extracted with 1000 ml of boiling dimethylformamide for 20 minutes, filtered hot, washed and dried. Thirteen and four-tenths grams of a red-shade yellow product are obtained. Upon analysis the following are the results:

| Calculated for $C_{34}H_{20}N_4O_4Ni$ | Found |
|---|---|
| Ni = 9.71 | 9.84 |
| N = 9.22 | 9.03 |
| C = 67.21 | 66.24 |
| H = 3.29 | 3.37 |

This analysis indicates the compound to be the chelate of the structural formula given as (V) above, wherein Me is nickel and each R is hydrogen.

The chelate is reddish-yellow in color and is found to possess outstanding outdoor durability when used as a pigment.

EXAMPLE 2

A. Synthesis of 3,6-dichloro-phenanthrene-9,10-diamine dihydrochloride

In this synthesis 45.0 grams of 3,6-dichloro-phenanthrene-9,10-quinone, 62.5 grams barium carbonate, and 56.5 grams hydroxylamine hydrochloride are heated in 4000 ml ethyl alcohol at reflux for five hours. The slurry is filtered hot and the presscake washed with alcohol. The filtrate is concentrated by evaporation to half its volume, cooled to 70°C. and 260 grams stannous chloride dissolved in 1200 ml concentrated hydrochloric acid is added over a 30-minute period, while maintaining the temperature below 80°C. The slurry is stirred for an additional one-half hour period while maintaining the temperature at 70° to 80°C., cooled to room temperature and filtered.

The presscake is washed first with concentrated hydrochloric acid, then with water, and dried at room temperature. The yield of white solid is 38.5 grams.

B. Synthesis of Schiff base from 2,4-dihydroxy-3-formylquinoline and the diamine of A Thirty-eight and one-half grams of the product of A, and 46.8 grams of 2,4-dihydroxy-3-formylquinoline are heated in 4000 ml of butanol at reflux for five hours. The hot slurry is filtered, the presscake washed with ethanol, and dried. The yield is 60.0 grams of a bright yellow solid.

C. Formation of nickel chelate

Thirty grams of the bright yellow Schiff base as prepared in B and 20.0 grams of nickel acetate tetrahydrate are heated under reflux in 3000 ml dimethylformamide for four hours. The slurry is filtered hot and the presscake washed free of nickel salts and dried. The product weighs 24.5 grams.

The 24.5 grams of product of C are pulverized and extracted with boiling dimethylformamide for twenty-five minutes, filtered hot, and the presscake washed until free of nickel salts and dried. A yield of 23.0 grams of a red-shade yellow product is obtained. Upon analysis, the following results are obtained:

| Calculated for $C_{34}H_{18}Cl_2N_4O_4Ni$ | Found |
|---|---|
| Ni = 8.60 | 8.89 |
| N = 8.29 | 8.11 |
| C = 61.48 | 58.19 |
| H = 2.67 | 2.72 |
| Cl = 10.51 | 10.0 |

This analysis shows that the chelate has a structure corresponding to that of formula (V), above, wherein Me is nickel and each R is chlorine.

EXAMPLE 3

A. Synthesis of 3,6-dibromo-phenanthrene-9,10-diamine dihydrochloride

Forty-six grams of 3,6-dibromo-phenanthrene-9,10-quinone, 56.5 grams of hydroxylamine hydrochloride and 62.5 grams of barium carbonate are heated at reflux in 2600 ml ethanol for five hours. The slurry is filtered hot and the presscake washed with alcohol. The filtrate is heated to 70°C. and 250 grams of stannous chloride dissolved in 1000 ml of concentrated hydrochloric acid is added over a 20-minute period with the temperature held at 80°C. The slurry is cooled to room temperature over a two-hour period and filtered, washed first with hydrochloric acid, and then with water, and dried. The product weighs 52.0 grams.

B. Synthesis of Schiff base from 2,4-dihydroxy-3-formylquinoline and the diamine of A To carry out the reaction, 26.0 grams of the product obtained in step A and 31.2 grams of 2,4-dihydroxy-3-formylquinoline are heated at reflux for five hours in 3000 ml of butanol. The slurry is filtered hot and the presscake washed with alcohol and dried. The yield of product is 40.0 grams.

C. Formation of nickel chelate

The 40 grams of product of step B and 20.8 grams of nickel acetate are heated at reflux in 3500 ml. dimethylformamide for four hours. The slurry is filtered hot, washed and dried. The yield is 23 grams.

The 23 grams of product from step C is pulverized and extracted with 1700 ml of boiling dimethylformamide for 20 minutes. The slurry is filtered hot, washed successively with dimethylformamide, alcohol, and water and alcohol, and dried at 60°C. The product is 21.5 grams of a red-shade yellow solid.

Analysis of this product shows the following:

| Calculated for $C_{34}H_{18}Br_2N_4O_4Ni$ | Found |
|---|---|
| Ni = 7.59 | 7.43 |
| N = 7.33 | 7.14 |
| C = 53.40 | 52.07 |
| H = 2.35 | 2.48 |
| Br = 20.95 | 18.9 |

This analysis shows the chelate has a structure corresponding to that of formula (V), above, wherein Me is nickel and each R is bromine.

EXAMPLE 4

A. Synthesis of Schiff base from 2-hydroxy-1-naphthaldehyde and phenanthrene-9,10-diamine For this reaction, 1.0 gram phenanthrene-9,10-diamine and 2.2 grams 2-hydroxy-1-naphthaldehyde are refluxed in a mixture of 200 ml ethanol and 200 ml of butanol for five hours. The slurry is filtered hot, and washed with a small volume of ethanol. The product is a bright yellow solid weighing 1.27 grams.

Analysis of this product shows:

| Calculated for $C_{36}H_{24}N_2O_2$ | Found |
|---|---|
| C = 83.72 | 82.04 |
| H = 4.65 | 4.59 |
| N = 5.42 | 5.84 |

B. Formation of nickel chelate

One gram of the product of A and 0.6 gram of nickel acetate tetrahydrate are heated in 100 ml of dimethylformamide at reflux for four hours. The slurry is filtered hot, washed, successively with alcohol, water and alcohol, and dried at 60°C. The yield of chelate is 0.99 gram.

EXAMPLE 5

Preparation of the chelate of Example 1 without isolation of the Schiff base

To carry out the reaction, 400 ml of dimethylformamide, 2.3 grams nickel acetate tetrahydrate and 3.0 grams 2,4-dihydroxy-3-formylquinoline are heated at reflux for one hour. After one hour, 2.0 grams phenanthrene-9,10-diamine dihydrochloride is added, and the reflux continued for an additional three and one-half hours. Immediately upon addition of the phenanthrene-9,10-diamine dihydrochloride a reddish-yellow solid precipitates out of solution. At the end of the reflux period, the slurry is filtered hot, washed with alcohol, then with water and alcohol, and dried at 80°C. The yield of the product is 2.2 grams.

EXAMPLE 6

Preparation of the chelate from 3,5-dibromosalicylaldehyde, phenanthrene-9,10-diamine dihydrochloride and nickel acetate For this preparation, six grams of nickel acetate tetrahydrate, and 10 grams of 3,5-dibromosalicylaldehyde are refluxed for two hours in 200 ml dimethylformamide. At the end of this time, five grams of phenanthrene-9,10-diamine dihydrochloride are added and the refluxing is continued for two hours. The hot slurry is then filtered, the precipitate washed successively with alcohol, water and alcohol and dried at 60°C. The yield of chelate is 5.4 grams.

For $C_{28}H_{14}N_2O_2Br_4Ni$, analysis shows:

| Found | Calculated |
|---|---|
| Ni = 7.01 | 7.35 |
| N = 3.65 | 3.55 |
| C = 44.6 | 42.75 |
| H = 1.95 | 1.77 |
| Br = 37.3 | 40.6 |

This example shows the formation of the tetrabromo-substituted chelate. The corresponding chloro-substituted chelate can be prepared by simple molar substitution of 3,5-dichlorosalicylaldehyde for 3,5-dibromosalicylaldehyde.

What is claimed is:
1. A Schiff base of structural formula:

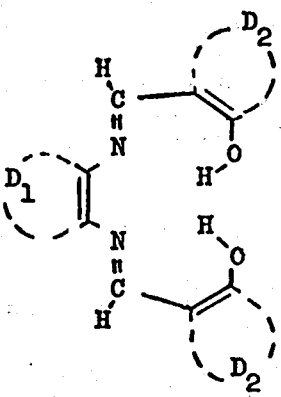

wherein $D_1$ represents the atoms necessary to complete a phenanthrene nucleus having the indicated nitrogen atoms attached to the 9,10-positions and $D_2$ represents the atoms necessary to complete a nucleus of the formula:

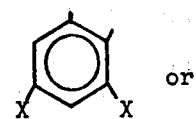 or

wherein X is chlorine or bromine.

* * * * *